(12) United States Patent
O'Mahony et al.

(10) Patent No.: US 7,671,974 B2
(45) Date of Patent: Mar. 2, 2010

(54) CUVETTE APPARATUS AND SYSTEM FOR MEASURING OPTICAL PROPERTIES OF A LIQUID SUCH AS BLOOD

(75) Inventors: John J. O'Mahony, Barna (IE); Xinrui Hou, Minneapolis, MN (US); Edwin B. Merrick, Stow, MA (US)

(73) Assignee: CHF Solutions Inc., Brooklyn Park, MN (US)

( * ) Notice: Subject to any disclaimer, the term of this patent is extended or adjusted under 35 U.S.C. 154(b) by 454 days.

(21) Appl. No.: 10/975,411

(22) Filed: Oct. 29, 2004

(65) Prior Publication Data

US 2005/0094127 A1    May 5, 2005

Related U.S. Application Data

(60) Provisional application No. 60/515,132, filed on Oct. 29, 2003.

(51) Int. Cl.
*G01N 33/48* (2006.01)
*G01N 21/05* (2006.01)

(52) U.S. Cl. .................... 356/39; 356/246; 356/436

(58) Field of Classification Search ......... 356/244–246, 356/39–42, 432, 436, 440–442
See application file for complete search history.

(56) References Cited

U.S. PATENT DOCUMENTS

| | | | | |
|---|---|---|---|---|
| 3,580,683 | A | * | 5/1971 | Schulkind .................. 356/414 |
| 3,728,032 | A | * | 4/1973 | Noll ........................... 356/246 |
| 3,740,156 | A | * | 6/1973 | Heigl et al. ................. 356/433 |
| 4,243,883 | A | * | 1/1981 | Schwarzmann ............ 250/343 |
| 4,784,768 | A | | 11/1988 | Mathieu |
| 5,231,464 | A | * | 7/1993 | Ichimura et al. ............ 356/477 |
| 5,247,434 | A | | 9/1993 | Peterson et al. |
| 5,312,535 | A | * | 5/1994 | Waska et al. ................ 204/603 |
| 5,366,630 | A | | 11/1994 | Chevallet |
| 5,670,050 | A | | 9/1997 | Brose et al. |
| 5,674,390 | A | | 10/1997 | Matthews et al. |
| 5,730,712 | A | | 3/1998 | Falkvall et al. |

(Continued)

FOREIGN PATENT DOCUMENTS

EP        0 274 178        7/1988

(Continued)

OTHER PUBLICATIONS

International Search Report dated Sep. 11, 2002.

(Continued)

*Primary Examiner*—Tarifur Chowdhury
*Assistant Examiner*—Tara S Pajoohi
(74) *Attorney, Agent, or Firm*—Nixon & Vanderhye P.C.

(57) ABSTRACT

A optical sensor for measuring tranmissive properties of a solution having: a cuvette body with an enclosed flow passage for the solution, wherein the flow passage further includes a solution inlet and a solution outlet and a cuvette between the inlet and outlet; a light source projecting light of a predetermined wavelength through the cuvette and solution flowing through the cuvette and to a light sensor, wherein the cuvette has inner wall surfaces opaque to the light of said predetermined wavelength, and the inner wall is in contact with the solution.

24 Claims, 8 Drawing Sheets

U.S. PATENT DOCUMENTS

| | | | |
|---|---|---|---|
| 5,762,805 | A | 6/1998 | Truitt et al. |
| 6,069,687 | A * | 5/2000 | Briggs ............ 356/39 |
| 6,284,131 | B1 | 9/2001 | Hogard et al. |
| 6,284,142 | B1 * | 9/2001 | Muller ............ 210/745 |
| 2001/0016699 | A1 | 8/2001 | Burbank et al. |
| 2001/0021817 | A1 | 9/2001 | Brugger et al. |
| 2001/0037079 | A1 | 11/2001 | Burbank et al. |
| 2001/0041892 | A1 | 11/2001 | Burbank et al. |
| 2002/0103453 | A1 | 8/2002 | Burbank et al. |
| 2002/0147423 | A1 | 10/2002 | Burbank et al. |
| 2003/0009123 | A1 | 1/2003 | Brugger et al. |
| 2003/0097087 | A1 | 5/2003 | Gura |
| 2003/0210390 | A1 * | 11/2003 | O'Mahony et al. ...... 356/218 |
| 2003/0218128 | A1 * | 11/2003 | Schulz ............ 250/252.1 |

FOREIGN PATENT DOCUMENTS

| | | |
|---|---|---|
| EP | 467805 | 1/1992 |
| EP | 0 990 444 A2 | 4/2000 |
| GB | 1 583 023 | 1/1981 |
| WO | WO 00/33053 * | 6/2000 |

OTHER PUBLICATIONS

Jonathan D. Sackner-Berstein, MD et al., "How Should Diuretic-Refractory, Volume-Overloaded Heart Failure Patients Be Managed?" The Journal of Invasive Cardiology, vol. 15, No. 10 (Oct. 2003), pp. 585-590.

Brian E. Jaski, MD et al., "Peripherally Inserted Veno-Venous Ultrafiltration for Rapid Treatment of Volume Overloaded Patients", Journal of Cardiac Failure, vol. 9, No. 3, (Jun. 2003), pp. 227-231.

* cited by examiner

CUVETTE APPARATUS AND SYSTEM FOR MEASURING OPTICAL PROPERTIES OF A LIQUID SUCH AS BLOOD

RELATED APPLICATION

This application claims priority to U.S. Provisional Application Ser. No. 60/515,132, filed Oct. 29, 2003, the entirety of which is incorporated by reference.

BACKGROUND OF THE INVENTION

The present invention is directed to an apparatus and system for measuring the constituent concentration value present in a liquid. This invention is applicable to sensing a hematocrit (Hct) level of blood in an extracorporeal circuit.

Renal Replacement Therapy (RRT) has evolved from the long, slow hemodialysis treatment regime of the 1960's to a diverse set of therapy options, the vast majority of which employ high permeability membrane devices and ultrafiltration control systems. Biologic kidneys remove metabolic waste products, other toxins, and excess water. They also maintain electrolyte balance and produce several hormones for a human or other mammalian body. An artificial kidney, also called a hemodialyzer or dialyzer, and attendant equipment and supplies are designed to replace the blood-cleansing functions of the biologic kidney. At the center of artificial kidney design is a semipermeable filter membrane that allows passage of water, electrolytes, and solute toxins to be removed from the blood. The membrane retains in the blood, the blood cells, plasma proteins and other larger elements of the blood.

Over the last 15 years, RRT systems have evolved into a subset of treatment alternatives that are tailored to individual patient needs. They include ultrafiltration, hemodialysis, hemofiltration, and hemodiafiltration, all of which are delivered in a renal care environment, as well as hemoconcentration, which is typically delivered in open heart surgery. RRT may be performed either intermittently or continuously, in the acute or chronic renal setting, depending on the individual patient's needs.

Ultrafiltration involves the removal of excess fluid from the patient's blood by employing a pressure gradient across a semipermeable membrane of a high permeability hemofilter or dialyzer. For example, removal of excess fluid occurs in hemoconcentration at the conclusion of cardiopulmonary bypass surgery. Hemodialysis involves the removal of toxins from the patient's blood by employing diffusive transport through the semipermeable membrane, and requires an electrolyte solution (dialysate) flowing on the opposite side of the membrane to create a concentration gradient. A goal of dialysis is the removal of waste, toxic substances, and/or excess water from the patients' blood. Dialysis patients require removal of excess water from their blood because they lack the ability to rid their bodies of fluid through the normal urinary function.

One of the potential risks to health associated with RRT is hypotension, which is an abnormal decrease in the patient's blood pressure. An abnormally high or uncontrolled ultrafiltration rate may result in hypovolemic shock, hypotension, or both. If too much water is removed from the patient's blood, such as might occur if the ultrafiltration rate is too high or uncontrolled, the patient could suffer hypotension and/or go into hypovolemic shock. Accordingly, RRT treatments must be controlled to prevent hypotension.

Alternatively, a patient may experience fluid overload in his blood, as a result of fluid infusion therapy or hyperalimentation therapy. Certain kinds of RRT machine failures may result in a blood fluid gain rather than fluid loss. Specifically, inverse ultrafiltration may result in unintended weight gain of a patient and is potentially hazardous. Uncontrolled infusion of fluid into the patient could result in fluid overload, with the most serious acute complication being pulmonary edema. These risks are similar in all acute and chronic renal replacement therapies (ultrafiltration, hemodialysis, hemofiltration, hemodiafiltration, hemoconcentration). Monitoring patients to detect excessive fluid loss is needed to avoid hypotension.

Rapid reduction in plasma or blood volume due to excessive ultrafiltration of water from blood may cause a patient to exhibit one or more of the following symptoms: hypovolemia-hypotension, diaphoresis, cramps, nausea, or vomiting. During treatment, plasma volume in the patient's blood would theoretically remain constant if the plasma refilling rate equaled the UF (ultrafiltration) rate and thus the hematocrit (Hct) would remain constant. However, refilling of the plasma is often not completed during a RRT session. The delay in refilling the plasma can lead to insufficient blood volume in a patient.

There appears to be a "critical" blood volume value below which patients begin to have problems associated with hypovolemia (abnormally decreased blood volume). Fluid replenishing rate is the rate at which the fluid (water and electrolytes) can be recruited from tissue into the blood stream across permeable walls of capillaries. Maintaining the critical blood volume ensures that blood volume is maintained relatively constant. Most of patients can recruit fluid at the rate of 500 to 1000 mL/hour. When patients are treated at a faster fluid removal rate, they begin to experience symptomatic hypotension.

Hypotension is the manifestation of hypovolemia or a severe fluid misbalance. Symptomatically, hypotension may be experienced by the patient first as light-headedness. To monitor patients for hypotension, non-invasive blood pressure monitors (NIBP) are commonly used during RRT. When detected early, hypotension resulting from the excessive loss of fluid is easily reversed by giving the patient intravenous fluids. Following administering fluids the RRT operator can adjust the ultrafiltration rate to make the RRT treatment less aggressive. Hct increases in proportion to blood volume loss barring blood loss and can be considered as a surrogate of blood volume. It is known to monitor Hct in the prevention the hypotension by decreasing the ultrafiltrate rate when Hct is seen to increase beyond a desired set value.

The wavelengths of light absorbed by a solute are a characteristic of the solute. Different solutes absorb light at different wavelengths. The concentration of a solute can be determined by measuring the light absorption at the wavelengths corresponding to the solute. If two solutes with different absorption spectra are in solution, their respective concentrations can be determined from the ratio of the light absorbed at two different wavelengths. Hemoglobin (Hb) absorbs less light of wavelength 940 nm (infra red light) than oxyhemoglobin $O_2Hb$, but absorbs more light of wavelength 660 nm (red light)—which is why oxygenated (arterial) blood appears redder than deoxygenated (venous) blood. The four types of hemoglobin have absorption spectra which differ from each other. By using four different wavelengths of light, each corresponding to a type of hemoglobin, the hemoglobin saturation can be determined from the levels of adsorption of light at each of the four wavelength ranges.

In invasive saturation monitoring, light beams only pass through blood and therefore hemoglobin oxygen saturation measurement is easy. The linearity of the Beer-Lambert law may be limited by chemical and instrumental factors, such as:

1) deviations in absorptivity coefficients at high concentrations (>0.01 M) due to electrostatic interactions between molecules in close proximity, 2) scattering of light due to particulates in the sample, 3) fluorescence or phosphorescence of the sample, 4) changes in refractive index at high analyte concentration, 5) shifts in chemical equilibrium as a function of concentration, 6) non-monochromatic radiation, (deviations can be minimized by using a relatively flat part of the absorption spectrum such as the maximum of an absorption band) and 7) stray light.

A sensor for measuring light absorption by a fluid may include a fluid passage, e.g., a blood tube, a light source and light detector defining a light path passing through the fluid passage, and a cuvette that is a structural body for the fluid passage between the light detector and source. It has been discovered that a cuvette body having transparent or reflective walls may improperly transmit light to the light detector. It has been shown that a cuvette body that has light paths not including the blood sample resulting from reflections or refractive body paths known as light pipes will give inaccurate optical transmission readings. It was noticed by the inventors that certain cuvette body materials, e.g., clear tubes, act as light pipes resulting in false transmittance readings. Some of the LED light instead of being transmitted through the liquid medium passed through the cuvette (blood tube) and made its way through the cuvette material to the photodiode. In the case of blood, high Hcts resulted in reflection and scattering with much of the resultant reflected LED lights making their way through the cuvette and to the photodiode via the cuvette wall. This resulted in erroneous transmittance readings which would lead to false Hct or the readings of other substance concentrations and other substance concentrations.

The cuvette blood passage should minimize light scattering and stray light that passes through the fluid passage and reaches the light detector. It has been discovered that clear walls of conventional blood tubes and filtrate tubes transmit reflected light intended to pass directly through the blood. The tubing acts as a light pipe that transmits the reflected light. The light transmitted by the walls of the blood tube may be sensed by the light detector intended to sense light flowing directed from a LED, through the blood cuvette and to the detector. By sensing the reflected light coming from the walls of the blood tube, the light detector may output a false signal that is improperly influenced by the light from the walls of the tube. Extraneous light paths therefore cause errors in measuring transmission and these errors are then propagated into the calculation of absorption. Accordingly, there is a need for a sensor for measuring the light absorption of blood flowing through a tube that does not transmit light into the sensor that has not passed through the blood.

SUMMARY OF INVENTION

There is a long felt need for a cuvette sensor that provides accurate measurements of absorption and transmittance in blood and other liquids. There is also a need for a cuvette that prevents this phenomenon of light being transmitted through the walls of the cuvette to the light detector. A cuvette has been developed having interior walls that do not reflect or transmit the LED light.

In the embodiment of the invention disclosed herein, three wavelengths of LED (Light Emitting Diode) were used 660 nm, 940 nm and 820 nm to measure the adsorption and transmittance of blood. These wavelengths were chosen because they are the best isospectic points for the measurement of oxygen saturation and Hct.

In one embodiment, the invention is a device for measuring optical properties of a solution comprising: a cuvette body having an enclosed flow passage for the solution, wherein said flow passage further comprises an solution inlet and a solution outlet and a cuvette between the inlet and outlet; a light source projecting light of a predetermined wavelength or several wavelengths through the cuvette and solution flowing through the cuvette and to a light sensor or sensors, and said cuvette having inner wall surfaces opaque to the light of said predetermined wavelength, and said inner wall in contact with the solution. The cuvette inner wall surface may further comprise opposite planer walls defining opposite sides of the flow passage in the cuvette. In addition, the inner wall surface may be planer walls defining opposite sides of the flow passage in the cuvette, wherein the planer walls are separated by a distance less than one quarter a width and/or height of each of the planer walls. Further, the inlet and outlet of the flow passage may be circular in cross section, wherein the cuvette further comprises opposite planer walls defining opposite sides of the flow passage in the cuvette, and the flow passage further comprise transition sections between the cuvette and each of said inlet and outlet. The cuvette body may be formed of a black plastic material such that the inner wall surfaces of the cuvette are black. The inlet, cuvette and outlet may be coaxial. Moreover, the cuvette may further comprise opposite apertures in said inner wall surface, and said apertures are optically aligned with the light source and light detector.

In another embodiment, the invention may be a hemoglobin sensor comprising: a cuvette body having an enclosed flow passage for the solution, wherein said flow passage further comprises an solution inlet and a solution outlet and a cuvette between the inlet and outlet; a light source projecting light of a predetermined wavelength through the cuvette and solution flowing through the cuvette and to a light sensor, wherein said predetermined wavelength has a wavelength in a range of about 800 to 930 nm; said cuvette having an inner wall surface opaque to the light of said predetermined wavelength, and said inner wall in contact with the solution.

In a further embodiment, the invention is a method for detecting blood concentrations in a blood carrying tube using a hemoglobin sensor having a cuvette, a light source, an optical path extending through the cuvette and a light sensor, said method comprising: connecting the tube to an inlet and to an outlet of the sensor; passing blood from the tube and through the cuvette, wherein the cuvette has an internal surface in contact with the blood and said internal surface is opaque to a light from the light source; projecting the light from the light source, through the cuvette and blood passing through the cuvette and to the light sensor, and based on the light detected by the light sensor determining whether a concentration of hemoglobin in the blood is above a threshold concentration level.

DETAILED DESCRIPTION OF THE INVENTION

A cuvette body has been developed which may be incorporated in an extracorporeal blood circuit system to measure particular concentrations of substances within blood. The cuvette is not limited to this particular application. The disclosed cuvette body includes a conduit for blood while facilitating measurement of specific blood properties.

Figure 1A:
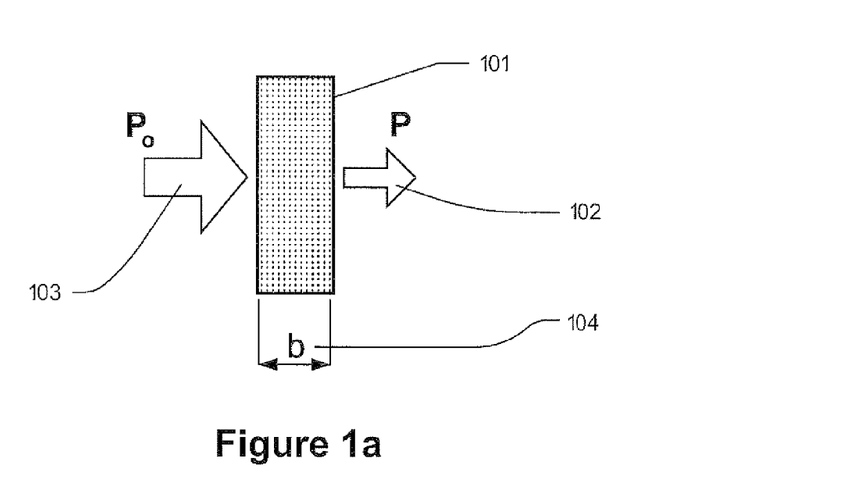
FIG. 1a is a diagram showing the absorption of light through an optical filter, such as a solution having solutes.

FIG. 1a is a diagram showing the absorption of light through an optical filter e.g., a blood passage and includes other processes that decrease surface reflectance and light scattering that can interfere with the measurement of blood properties.

The Beer-Lambert law (also called the Beer-Lambert-Bouguer law or simply Beer's law) is a linear relationship between absorbance and the concentration of an absorber of electromagnetic radiation. The general Beer-Lambert law is usually written as:

$$A = a_\lambda \times b \times c$$

where A is the measured absorbance, a $\lambda$ is a wavelength-dependent absorptivity or extinction coefficient, b 104 is the path length, and c is the analyte concentration of the solution 101 having light absorbing solutes. When working in concentration units of molarity, the Beer-Lambert law may be expressed as:

$$A = \epsilon_\lambda \times b \times c$$

where $\epsilon \lambda$ is the wavelength-dependent molar absorptivity coefficient with units of $M^{-1}cm^{-1}$. The $\lambda$ subscript is often dropped with the understanding that a value for $\epsilon$ is for a specific wavelength. If multiple species that absorb light at a given wavelength are present in a sample, the total absorbance at that wavelength is the sum due to all absorbers:

$$A = (\epsilon_1 \times b \times c_1) + (\epsilon_2 \times b \times c_2) + \ldots$$

where the subscripts refer to the molar absorptivity and concentration of the different absorbing species that are present.

Experimental measurements are usually made in terms of transmittance (T), which is defined as:

$$T = \frac{P}{P_0}$$

where P 102 is the power of light after it passes through the sample and Po 103 is the initial light power. The relation between A and T is:

$$A = -\log(T) = -\log\left(\frac{P}{P_0}\right)$$

Beer-Lambert Law describes absorption of light in a fluid $$Po = Pe^{-bc\epsilon}$$

Where, $\epsilon$ is the extinction coefficient which is the fraction of light lost to scattering and absorption per unit distance in a participating medium. It is the sum of the absorption coefficient and the scattering coefficient. The standard unit of the extinction coefficient is fraction per meter ($m^1$).

Figure 1B:
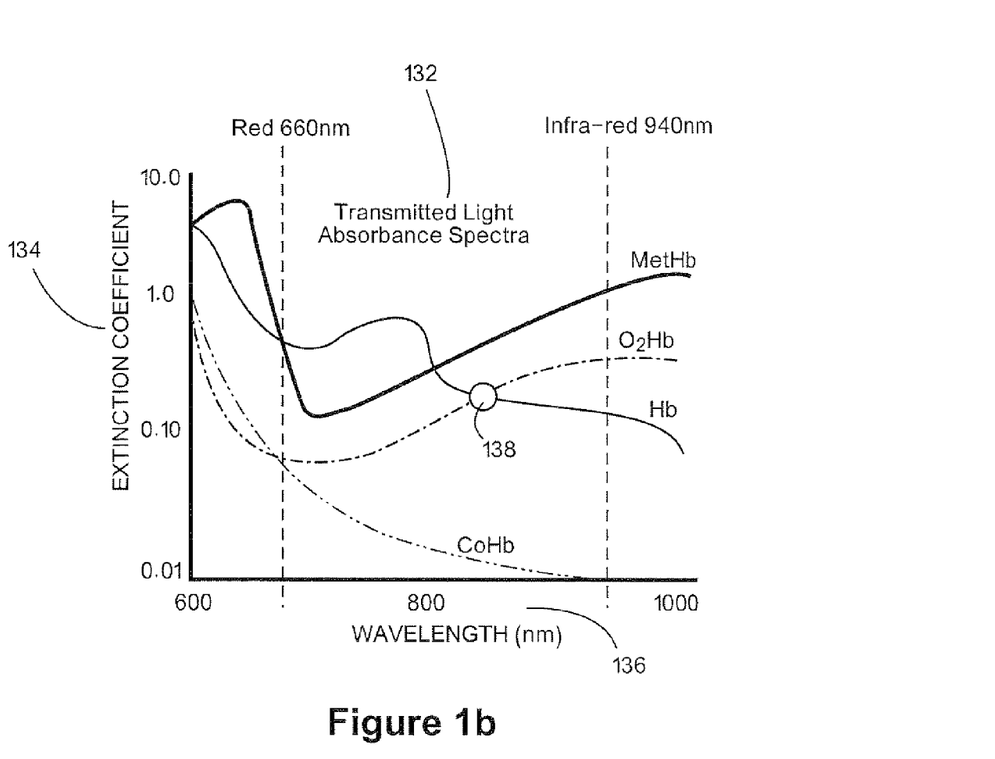
FIG. 1b is a chart of the extinction coefficients for various wavelengths in blood components.

FIG. 1b is a chart 132 of the extinction coefficients for various wavelengths in blood hemoglobin such as MetHb, $O_2Hb$, Hb and CoHb. The chart 132 shows the light adsorption 134 (in terms of molecular extinction coefficient) of different types of hemoglobin at various wavelengths 136 between 600 to 1000 nanometers (nm). The molecular extinction coefficient 134 is a property of each hemoglobin type at each wavelength. The different types of hemoglobin that are charted 132 include hemoglobin (Hb) without an oxygen molecule (also referred to as de-oxy hemoglobin) and hemoglobin ($O_2Hb$) combined with an oxygen molecule (oxy-hemoglobin), which are the two most common forms of hemoglobin. De-oxy hemoglobin and oxy-hemoglobin are sensed by a cuvette sensor monitoring the filtrate from a blood ultra-filtration filter. Hemoglobin in the filtrate indicates a failure of the ultra-filtration filter. The other types of hemoglobin charted in 132 (CoHb) (which generally occurs in the blood of fire victims, and cyan-hemoglobin and meth-hemoglobin (MetHb) (which generally occur in the blood of poison victims). For purposes of measuring oxygen concentration and Hct, the optical properties of these extraordinary types of hemoglobin, i.e., carboxy-, cyan- and meth-hemoglobins, can be ignored.

The two most common hemoglobins (oxy and de-oxy —$O_2Hb$ and Hb) have identical light absorption characteristics at 800 nm, as is shown in the chart 132 at point 138. The light adsorption of oxy-hemoglobin and de-oxy hemoglobin is substantially the same for wavelengths from 800 nm to 930 nm, and from 250 nm to 600 nm (not shown on FIG. 1b). The cuvette sensor senses light at or around 820 nm in order to be equally responsive to oxy- and de-oxy hemoglobins flowing in the filtrate tube. The detector exploits the fact that the extinction coefficients of oxy and de-oxy hemoglobin are substantially equal in the range of wavelengths from 930 nm to 800 nm. By emitting a light beam in this range, the detector is relatively insensitive to blood oxygenation. Commercially available solid state light sources and detectors that are responsive to 820 nm wavelengths may be selected for use in the sensor.

The cuvette sensor utilizes a light emitting diode (LED) and a matched light detector, e.g, photodiode, that have narrow spectral emission and detectivity curves. Three LED with different wavelengths were chosen to measure Hct and oxygen saturation. A 820 nm LED was chosen for measuring Hct and 660 and 940 nm LEDs were chosen for measuring oxygen saturation. Standard electrical techniques were used to sequence the LEDs. The 820 nm wavelength of light is equally absorbed by oxy- and de-oxy hemoglobin.

The Hct and oxygen saturation sensor may also include a modulated drive (see FIG. 2) for the LEDs and a synchronous demodulator that are arranged in the cuvette body to further reduce the responsiveness of the detector to ambient light interference. The sensor in effect only amplifies the difference between a photo detector reading when a particular LED is powered on and when all LEDs are powered off.

Figure 2:
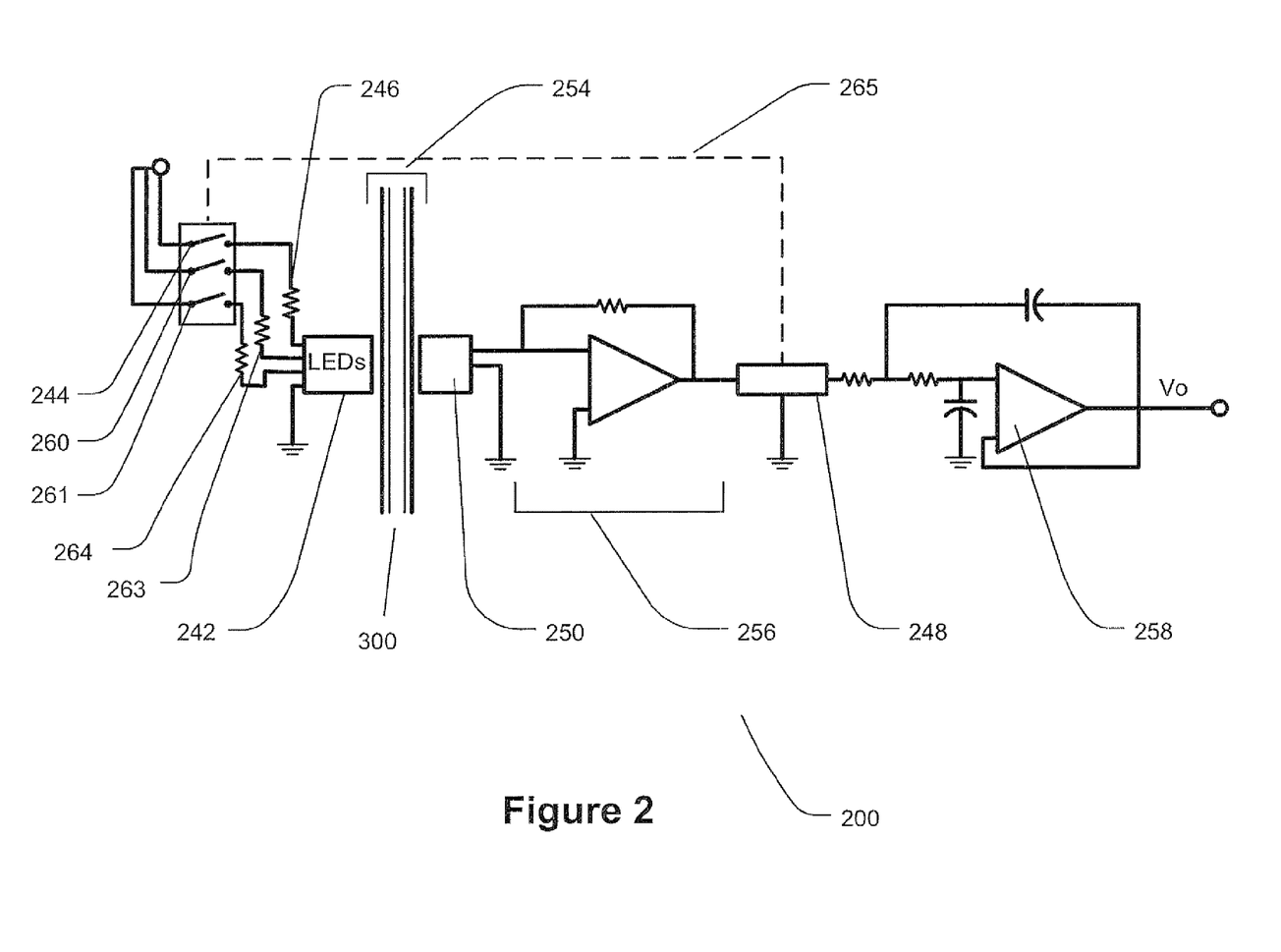
FIG. 2 is a block diagram of an exemplary electronic drive circuit for a LED drive circuit and optical sensor in the sensor.

FIG. 2 is a block diagram of an exemplary drive circuit 200 for a LED and optical sensor in a cuvette sensor. The driving circuit for the LEDs 242 includes switches 244, 260, 261 each in series with a respective resistor 246, 263, 264. The switches may be operated by a square wave or other duty cycle, at a frequency in a range of 100 to 10,000 Hz for example. During each duty cycle a different LED 242 is powered, by turning one switch on and the other two switches off. Each LED is powered every fourth cycle. The current supplied to the LED drive circuit is an alternating current (AC) drive of a particular phase and frequency.

The demodulator 248 for the light sensor 250 is operated at the same frequency and phase as the LED drives. The demodulator 248 is coupled 265 to the same drive signal as the switches 246, 263 264 for the LEDs 242 to ensure that the demodulator is synchronized with the LED drives. The light emitted from each LED is detected by the photodetector 250. Because ambient light does not have a same frequency as the demodulator 248, the effect of ambient light is subtracted from the LED using the synchronous demodulator 248.

The cuvette body 254 includes a cuvette blood passage 300 containing blood with a particular Hct and oxygen saturation. The blood passage 300 is in the optical path between the LEDs and photo diode. Light from the LEDs passes through the blood passage 300 and impinges on photodiode sensor 250. The photodiode produces a voltage-current signal in response to the light. The signal is amplified by a trans-impedance amplifier 256.

The gain of the trans-impedance amplifier 256 produces a usable signal that is demodulated 248 and output to a filter 258 such as, for example, 4.0 volts, when the optical path is not attenuated. The filter 258 removes the synchronous drive frequency, which is the common duty cycle applied to both the switch 244 and demodulator 258. The combination of the duty cycle applied to the LEDs and demodulator and filter effectively filters out from the sensor signal effects of ambient light. The output (V0) of the filter is a voltage proportional to the intensity of the light energy originating at the LEDs, traversing the path 300 through the cuvette, and impinging on the photodiode 250. The LEDs may be selected to each emit a particular wavelength, such as 660, 820 and 940 nm. Similarly, the photodiode may be selected to be most responsive to the wavelength(s) emitted by the LEDs resulting in the photodiode being less sensitive to other spectra.

The alternating current drive frequency may be selected to be other than line frequency, e.g., not 60 cycles per second. The demodulator 248 may be activated on the same cycle frequency as the drive frequency of the LED. By employing a demodulation scheme that responds to the frequency and phase of the driver of the LED source, the demodulator is desensitized to ambient light. Extreme ambient light may overdrive the first trans-impedance amplifier, even if the demodulator is driven at the same frequency as the LED. However, extreme ambient light is blocked from the photodiode 250 by the housing for the cuvette. To minimize reflecting ambient light towards the photodiode, the optical devices and housing are opaque and non-reflective at the operative wavelength of the LED, such as 660 to 940 nm. This makes it difficult for stray beams of spectra close to those output by the LEDs to penetrate through to the photodetector.

Figure 3A:
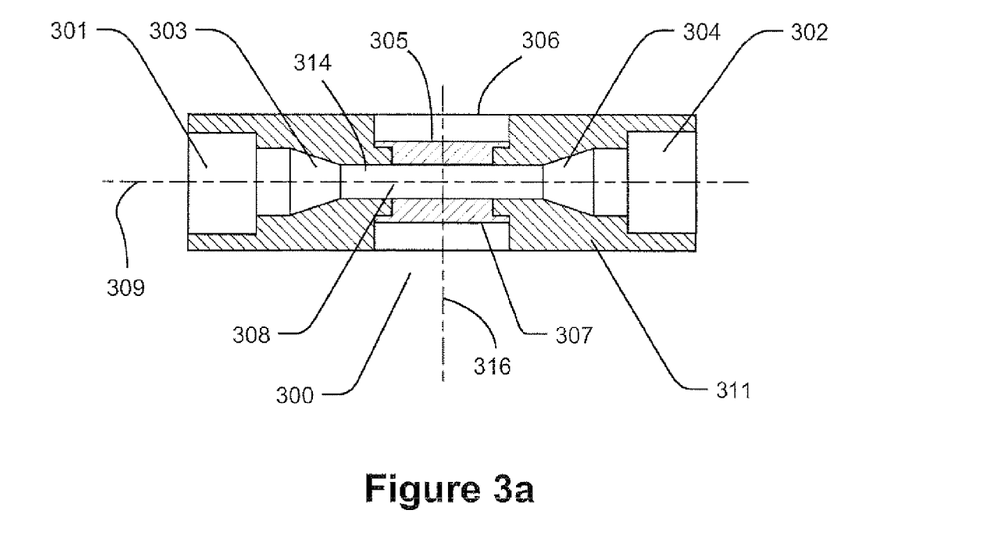
FIGS. 3a and 3b show elevation and plan cross-sectional views respectively of an exemplary cuvette body.
Figure 3B:
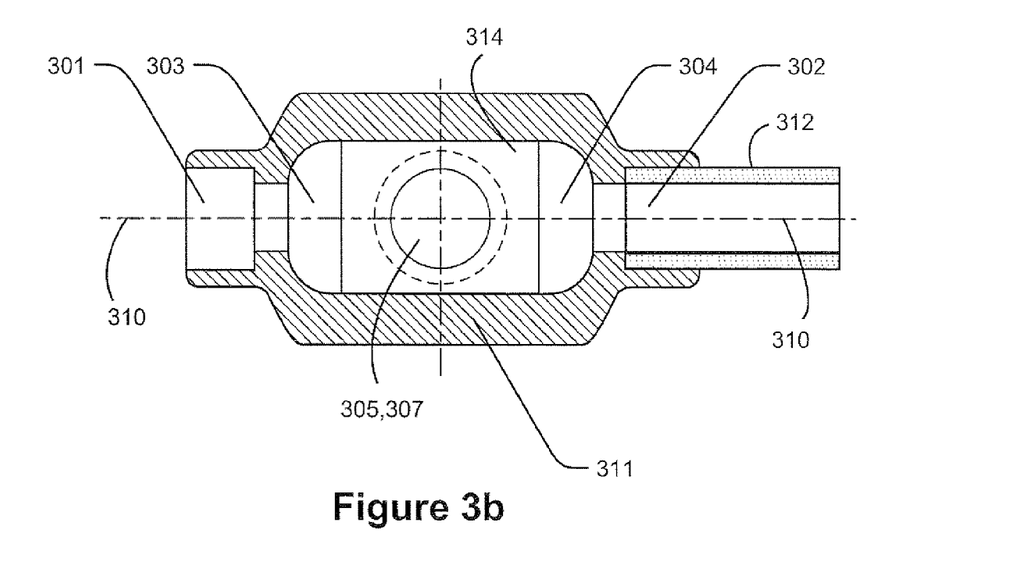

FIGS. 3a and 3b show an elevation and plan cross-sectional views of an exemplary cuvette body. FIGS. 3a and 3b are orthogonal views of the cuvette body. FIG. 3a shows the cuvette body in a cross-section taken along solution centerline 310 of FIG. 3b. FIG. 3b shows the cuvette body in a cross-section taken along centerline 309 of FIG. 3a (which is the same as centerline 310 but rotated by 90 degrees). The cuvette body 311 has a blood passage 314 extending along centerline 310 and between a blood inlet 301 and outlet 302. An inlet blood tube 312 may be connected to inlet 302 and an outlet blood tube may be connected to the outlet 301. The cuvette blood passage 314 is surrounded by the opaque walls of the cuvette. The cuvette inside walls may be substantially planer and separated by a narrow gap of, for example, between 0.1 mm and 3 mm where the transmitted LED lights are allowed to pass through. The height and width of the flat inside walls of the cuvette are substantially greater than the gap between the walls. For example, the height and width of the walls is at least four times the gap between the walls and can be designed as a function of the allowable cuvette pressure drop.

The flat inner walls of the cuvette have apertures 306 to receive optical disks 305, 307 aligned with the light path through the cuvette. Two transparent disks 305 and 307 are mounted in the cuvette body and are on opposite sides of the passage 314. The front face of the disks may be in the same plane as the inside surface of the cuvette inner walls. The front face of the disks are in contact with the blood flow. Light passes through: the disk 305 adjacent a light source, e.g., LEDs 242, the cuvette and the blood flowing through the cuvette, and the opposite disk 307 adjacent the light detector 250. Light that is scattered or reflected by hemoglobin Blood conduit tubes 312 may be glued to the inlet 301 and outlet 302 of the cuvette. The inside surfaces of the cuvette blood passage minimize flow perturbations to the medium flow by presenting a smooth inner surface without sudden expansions and contractions of internal geometry, which in the case of blood may result in the formation of clots. Eddies and separation zones are minimized in the passage. The passage 314 transferring the blood to the cuvette is tapered 303 to a 1 mm wide slot 308 with flat parallel walls between the opal glass diffusers 305 and 307. The opal diffusers are used as the light path between the LEDs and photo detector. The other end of the passage 314 is a circular tapered tubing 304. The body of the cuvette is made of polymer opaque to the LED wavelengths 660, 820 and 940 nm, i.e. almost any colored polymer for instance white or black PVC (Poly vinyl chloride).

Figure 4:
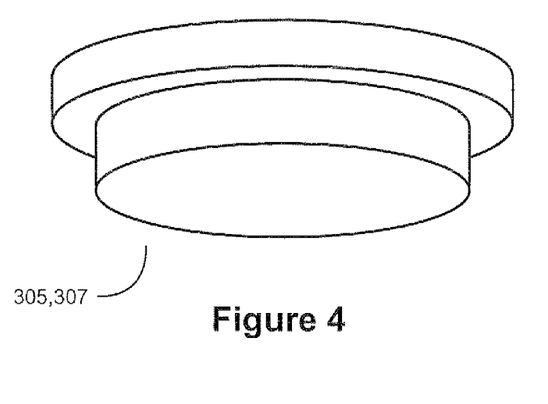
FIG. 4 is a detailed perspective view of a transparent disk for the cuvette body.

FIG. 4 shows a more detailed perspective view of the transparent opal disk 305, 307 which is press fit into the cuvette body 311. The disk is may be made from a polymer transparent to all the LED wavelengths, e.g., acrylic, polysulphone, transparent PVC or PC (Polycarbonate). Not all grades of these materials will be completely transparent to the LED wavelengths so it is important to measure the transmittance and determine the attenuation of the spectrum signal of the cuvette body material.

Figure 5:
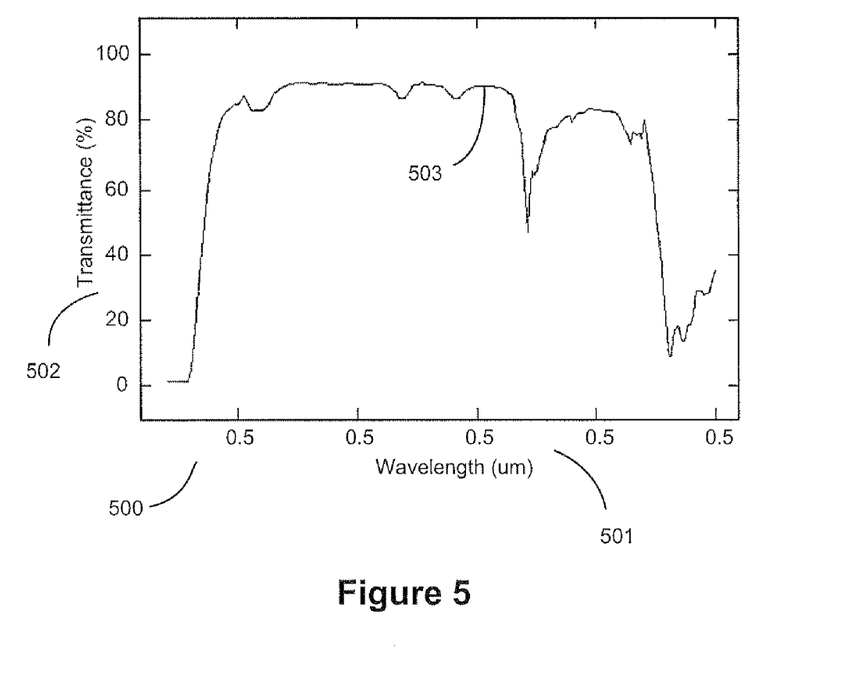
FIG. 5 is a graph of the transmittance of a particular grade of PVC cuvette body material at various wavelengths.

FIG. 5 shows a graph 500 of the transmittance 502 of a particular grade of PVC at various wavelengths 501. Between 80% and 90% of the light transmitted at wavelengths between 660 nm to 940 nm (0.6 to 0.94 µm) will be transmitted 503 through this grade of PVC. This makes such a material ideal for the transparent disk 305 windows of the cuvette.

Figure 6:
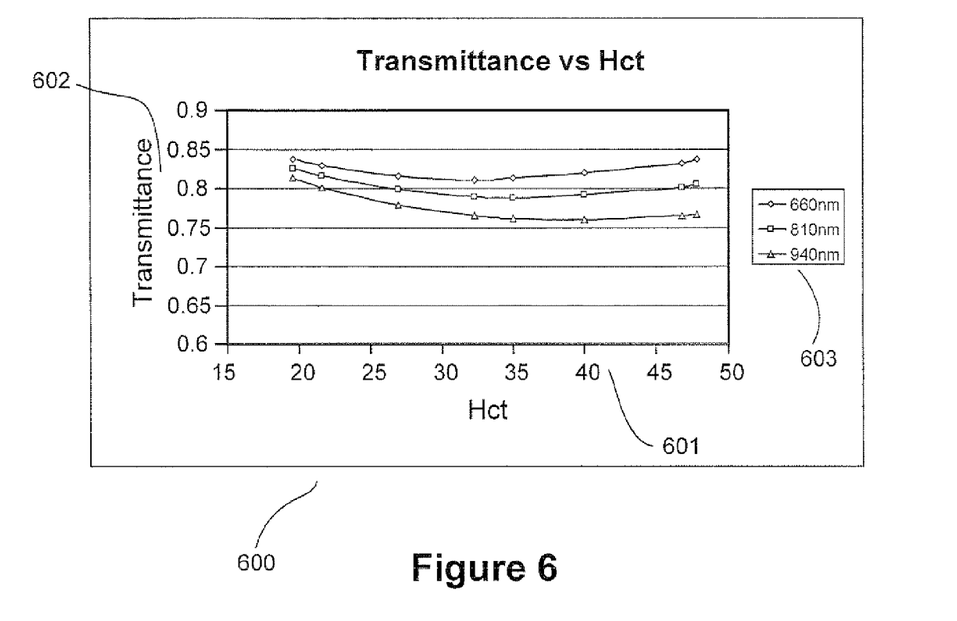
FIG. 6 is a chart of the transmittance results of the cuvette containing blood at varying Hct levels when the cuvette body is made of a transparent polycarbonate material.

FIG. 6 shows the transmittance results of the cuvette 300 when the cuvette body is made of a transparent polycarbonate material which allows the cuvette to act as a light pipe. The horizontal axis shows the percentage of Hct 602 in the blood flowing through the cuvette and the vertical axis shows the transmittance 601 of the three LED wavelengths 660 nm, 820 nm and 940 nm 603 passing through cuvette and blood. The sensor was calibrated to show a transmittance of 1.0 when saline was passed through the cuvette. As the Hct levels were increased from 20% to 33% the transmittance of each of the LED wavelengths 603 decreased. With Hct values greater than 33%, the transmittance values increase. The distance between the planar surfaces of 305, 307 of FIG. 3a was 1.0 mm in this test.

Figure 7:
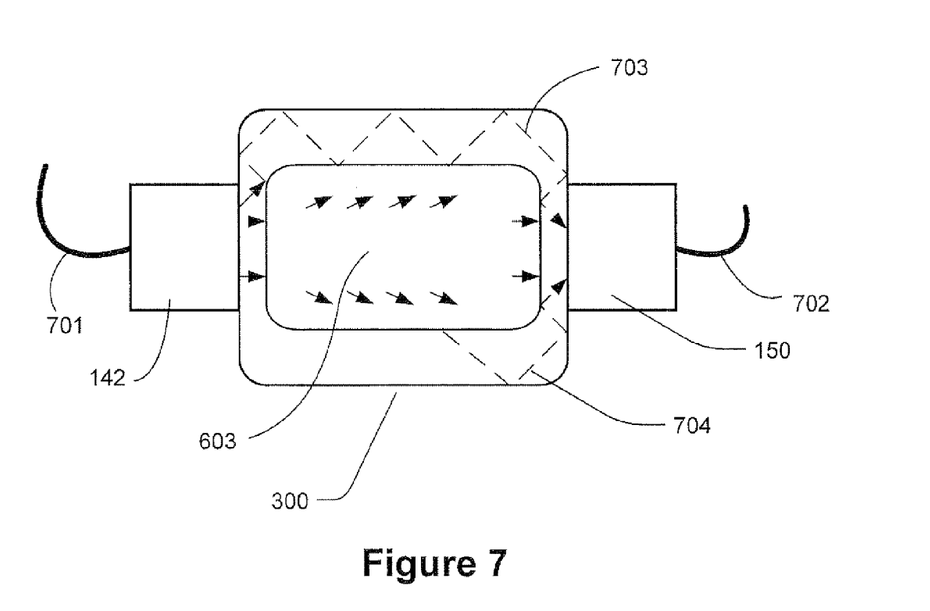
FIG. 7 is a diagram of a cuvette with light reflections indicated through the cuvette body.

FIG. 7 is a diagram of a cuvette with light reflections indicated. The cuvette body 300 is shown in cross-section with the LEDs 142 and associated LED control line 701, and the photodiode 150 and associated photodiode output line 702, wherein the LED and photodiode are on either side of the blood passage 603. As the Hct increases, the reflectance and diffusion of the blood 603 increased resulting in the transparent cuvette, e.g., a blood tube acting as a light pipe and LED light 703, 704 making its way to the photodiode 150 through paths other than straight through the blood passage. The light passing through the transparent walls of the blood tube is sensed by the photo detector. As the Hct increased the level of reflection increases resulting in false high transmittance readings by the cuvette.

Figure 8:
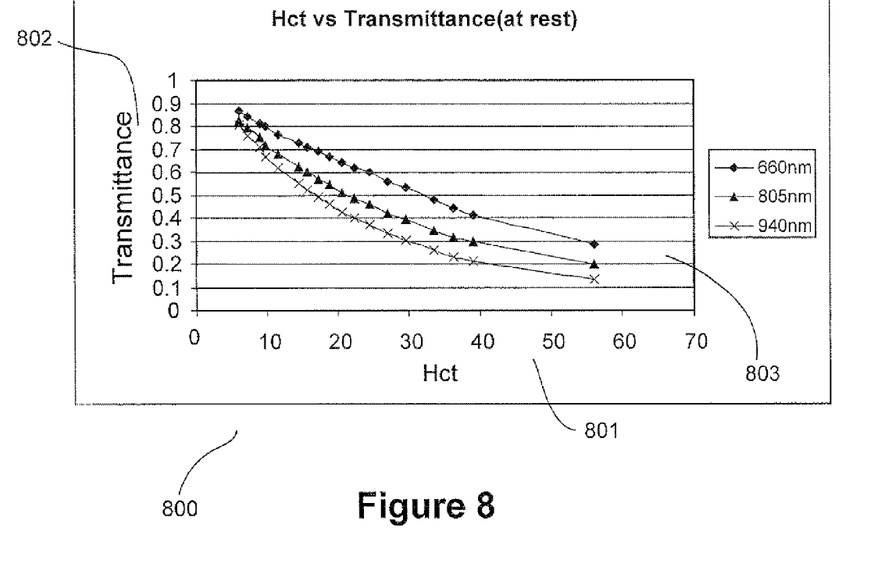
FIG. 8 is a chart showing the transmittance results of the cuvette when the cuvette body was made from a non-transparent PVC material.

FIG. 8 shows the transmittance results of the cuvette 300 when the cuvette body, including blood passage, was made from a non-transparent PVC material. The horizontal axis shows the percentage of Hct 802 flowing through the cuvette and the vertical axis shows the transmittance 801 of the three wavelengths 660 nm, 820 nm and 940 nm 803 passing through cuvette and blood sample. The sensor was calibrated to show a transmittance of 1.0 when saline was passed through the cuvette. As the Hct levels were increased from 5% to 60% the transmittance of each of the LED wavelength 803 decreased as expected.

Figure 9:
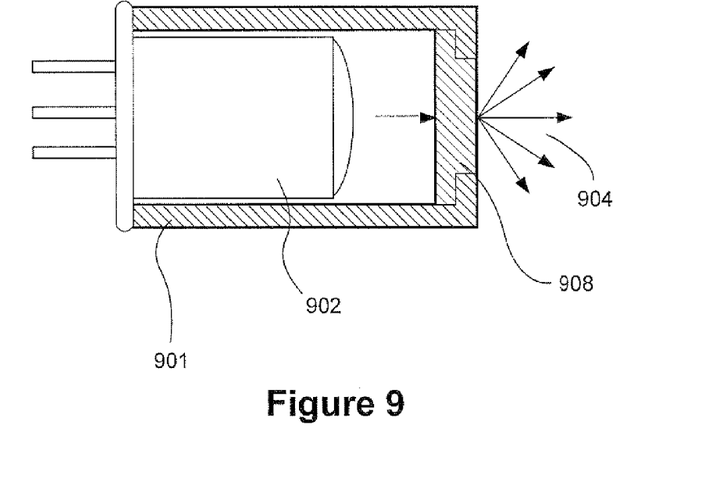
FIG. 9 is a diagram, shown in cross-section, of a LED housing for the cuvette.

FIG. 9 shows a more detailed drawing of the LED housing that is fitted into the cuvette body adjacent the blood passage. The body of the housing 901 is also made from a nontransparent material for the wavelengths being transmitted such as black PVC. The LEDs 902 include a 660 nm LED, an 820 nm LED and a 940 nm LED. A diffuser of opal glass 908 fitted in the LED housing creates a more even distribution of light being transmitted to the blood passage. The photodiode is housed in a similar housing 901 made of a nontransparent material to minimize the amount of ambient light from entering hitting the photodiode. A diffuser of opal glass similar to 908 fitted in front of the photodiode may also be used to create a more even distribution of light hitting the photodiode. The outside face of the opal glass 908 is fitted to the outside surface of the transparent disk 305, 307 FIG. 3a. This provides the light path for the various wavelengths parallel to the axis 316. The various wavelengths are turned on and off in sequence and pass through the opal glass diffuser, through the transparent disks 305, through the test sample in the conduit 314, through transparent disks 307, through the photodetector opal glass before hitting the photodetector.

Figure 10:
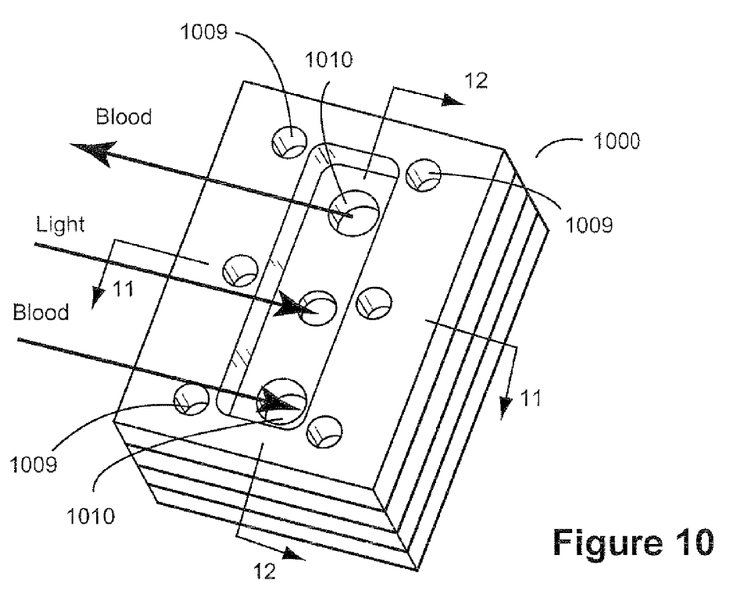
FIG. 10 is a perspective view of a second embodiment of the cuvette body.
Figure 11:
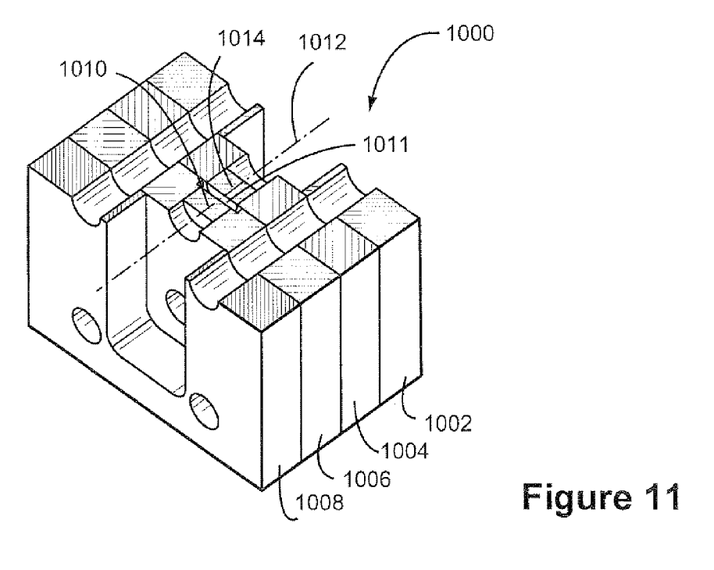
FIG. 11 is a perspective view of cuvette shown in FIG. 10, shown partially in cross-section along line 11-11 in FIG. 10.
Figure 12:
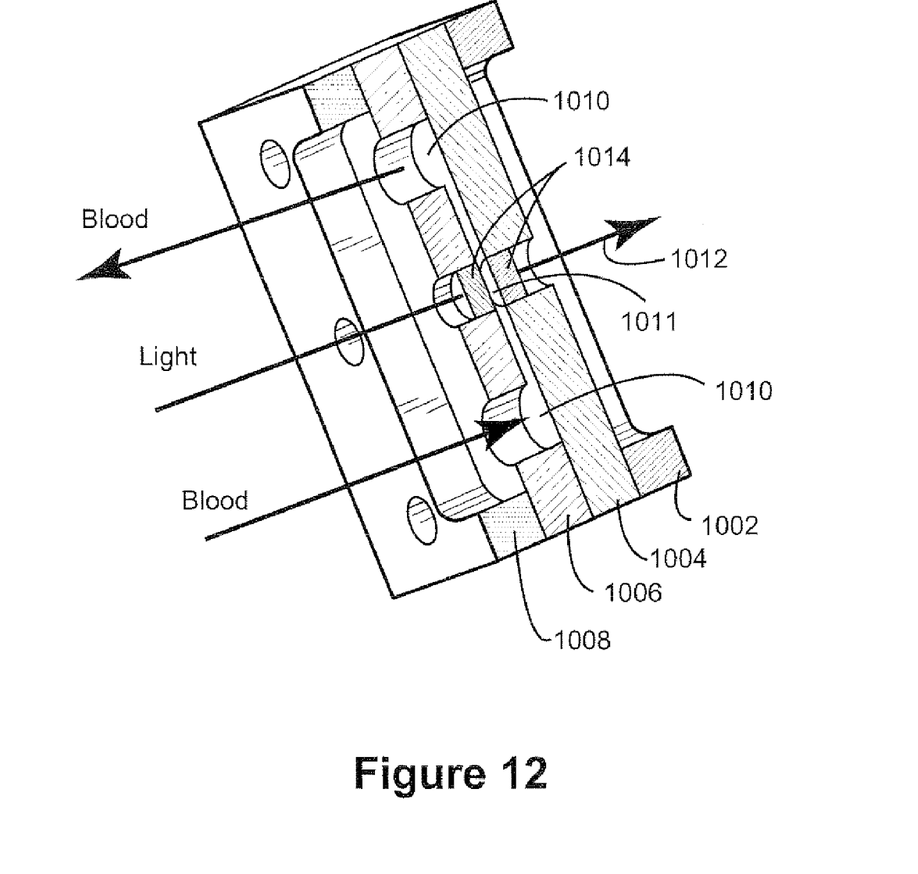
FIG. 12 is a perspective view of cuvette shown in FIG. 10, shown partially in cross-section along line 12-12 in FIG. 10.

FIGS. 10 to 12 show a second embodiment of a cuvette body 1000. The body is a lamination of four opaque plates 1002, 1004, 1006 and 1008 that define an internal blood passage 1010 having a cuvette 1011 which includes a transparent light path through the transparent disks 1010 and 1014. A light passage 1012 is orthogonal to and passes through the cuvette 1011. The outer plates 1002 and 1008 may be made of aluminum and are provided for structural support of the body 1000. The inner plates 1004, 1006 may be black polycarbonate. The four plates may be sandwiched together by bolts or screws extending through the outer holes 1009 in each of the plates. The inner plates 1004, 1006 prevent the reflection of light in the blood passage 1010 and block light that does not pass through the light passage 1012. The blood passage 1010 includes a blood inlet and outlet 1011 shown in FIG. 10 that extend to a narrow cuvette 1011 extending along line 12-12 of FIG. 10 and shown lengthwise in FIG. 12. The blood flow path of blood through the cuvette may be orthogonal to the flow path of the inlet and outlet to the cuvette body.

The inner walls of the cuvette passage 1011 are opaque and do not transmit LED light. The inner walls are in contact with the blood flowing through the cuvette. The light passage 1012 includes a pair of optical disks 1010 and 1014 on opposite sides of the blood cuvette passage. The disks are orthogonal to the cuvette 1011 portion of the light passage. The optical disks may be diffusive or clear or other suitable optical material. Light 1012 is transmitted trough the blood in the cuvette 1011 and does not leak within the inner plates 1004, 1006 that form the cuvette.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An optical sensor for determining optical properties of a solution, said sensor comprising:
a cuvette body having an enclosed flow passage for the solution, wherein the flow passage further comprises a solution inlet and a solution outlet and a cuvette between the solution inlet and the solution outlet;
opposite sidewalls of the cuvette body included in the flow passage and between the solution inlet and the solution outlet;
a light source projecting light of a predetermined wavelength along a light path through the cuvette to a light sensor, wherein the solution flows through the flow passage of the cuvette body;
transparent windows in each of the opposite sidewalls to the cuvette body and aligned with the light path, wherein a width of each transparent window is narrower than a width of the sidewall, and wherein each sidewall has a inner sidewall surface in contact with the solution and the inner sidewall surface has a length in a direction of flow and the length is longer than the width of the inner sidewall surface of the sidewall, and
wherein the inner sidewall surface is opaque to the light, and wherein each of said transparent windows have a perimeter surrounded by the opaque inner sidewall surface.

2. The device of claim 1 wherein said opposite sidewalls are planar walls defining opposite sides of the flow passage in the cuvette body and the transparent windows are embedded in the planar walls.

3. The device of claim 1 wherein said transparent windows are each a transparent opal disk.

4. The device of claim 1 wherein the solution inlet and the solution outlet of the flow passage are each circular in cross section, and said flow passage further comprises transition sections between the cuvette and each of said solution inlet and said solution outlet.

5. The device of claim 1 wherein the cuvette body is formed of a black plastic material.

6. The device of claim 1 wherein the inner sidewall surfaces of the cuvette are black.

7. The device of claim 1 wherein the solution inlet, flow passage and solution outlet are coaxial.

8. The device of claim 1 wherein the transparent windows are positioned in opposite apertures in said inner sidewall surfaces, and said apertures are optically aligned with the light source and light sensor.

9. The device of claim 8 further comprising optical diffusers fitted into each of said apertures.

10. The device of claim 8 further comprising transparent opal disks fitted into each of said apertures.

11. The device of claim 1 wherein a solution flow direction through the cuvette is orthogonal to a solution flow direction through the solution inlet and the solution outlet.

12. The device of claim 1 wherein the cuvette body further comprises a lamination of opaque plates having opposing slots defining the cuvette.

13. The optical sensor of claim 1 wherein the solution inlet and the solution outlet are perpendicular to the flow passage.

14. The optical sensor of claim 13 wherein the projected light is parallel to the solution inlet and solution outlet.

15. The optical sensor of claim 1 wherein the sidewalls are substantially planar.

16. An optical sensor for determining optical properties of a solution, said sensor comprising:
   a cuvette body having an enclosed flow passage for the solution, wherein the flow passage further comprises a solution inlet and a solution outlet and a cuvette between the solution inlet and the solution outlet;
   opposite sidewalls of the flow passage, included in the cuvette body and extending between the solution inlet and the solution outlet;
   a light source projecting light of a predetermined wavelength along a light path through the cuvette to a light sensor, wherein the solution flows through the flow passage of the cuvette body;
   transparent windows in each of the opposite sidewalls of the flow passage and aligned with the light path, wherein a width of each transparent window is narrower than a width of the sidewall, each of the opposite sidewalls has a length in a direction of flow and said length is perpendicular to the width of the sidewall, the length of each sidewall is longer than the width of the sidewall, and said sidewalls are separated from each other by a distance less than one quarter of the width of each of the sidewalls, and
   said cuvette body having an inner sidewall surface on each of the opposite sidewalls, wherein the inner sidewall surface is opaque to the light, and said inner sidewall surface is in contact with the solution, and wherein each of said transparent windows have a perimeter surrounded by the opaque sidewall surface.

17. A hematocrit detector for extracorporeal blood comprising:
   a cuvette body having an enclosed flow passage for a solution including the extracorporeal blood, wherein said flow passage further comprises a solution inlet, a solution outlet and a cuvette between the solution inlet and the solution outlet;
   opposite sidewalls of the flow passage, are included in the cuvette body and are between the solution inlet and the solution outlet;
   a light source projecting light of a predetermined wavelength through the cuvette body, the solution flowing through the flow passage and to a light sensor, wherein said predetermined wavelength has a wavelength in a range of about 800 to 930 nm,
   the opposite sidewalls each having a transparent window in the cuvette body, wherein each sidewall of the flow passage has a length in a direction of flow and the length is longer than a width of the sidewall, and
   said cuvette has an inner sidewall surface of each of the opposite sidewalls opaque to the light of said predetermined wavelength, said inner wall surface is in contact with the solution, and
   wherein the transparent windows are aligned with the light source and the light sensor, and each of said transparent windows is narrower than the width of the sidewall and has a perimeter surrounded by the inner wall surface.

18. A hematocrit detector as in claim 17 wherein the light sensor is responsive substantially only to the wavelength of the light of the predetermined wavelength.

19. A hematocrit detector as in claim 17 wherein the light source is cyclically turned on and off at a defined rate, and, during each cycle, said light sensor generates a first signal, in response to detecting the light, when the light source is on and a second signal when the light source is off.

20. A method for detecting blood concentrations in a blood carrying tube using a hematocrit detector having a cuvette, a light source, an optical path extending through the cuvette and a light sensor, said method comprising:
   a. connecting the blood carrying tube to blood inlet and to blood outlet of the detector;
   b. passing blood from the blood carrying tube and through the blood inlet, a blood flow passage in the cuvette and the blood outlet of the detector, wherein the blood flow passage has opposite sidewalls included in the cuvette, and each of the opposite sidewalls is opaque to light from the light source;
   c. while passing the blood through the blood flow passage in the cuvette, projecting the light from the light source through a pair of windows in each of the opposite sidewalls and to the light sensor, wherein the windows each have a width narrower than the sidewall including the window and the windows each have a perimeter surrounded by the the sidewall including the window, and
   d. measuring the light projected through the pair of windows and detected by the light sensor to determine a concentration of hematocrit in the blood.

21. A method as in claim 20 further comprising determining a concentration of hemocrit in the blood based on the measured light, and automatically ceasing blood flow through the blood carrying tube if a concentration of hematocrit in the blood is above a predetermined concentration level.

22. A method as in 20 further comprising determining a concentration of hemocrit in the blood based on the measured light, and automatically ceasing a filtration of the blood if the concentration of the hematocrit is above a predetermined concentration level.

23. A method as in claim 20 further comprising determining a concentration of hemocrit in the blood based on the measured light, and automatically reducing a filtration of the blood if the concentration of the hematocrit is above a predetermined concentration level.

24. A method as in claim 20 wherein said light has a wavelength in a range of about 800 to 930 nm.

* * * * *